United States Patent [19]

Hori et al.

[11] Patent Number: 5,014,553

[45] Date of Patent: May 14, 1991

[54] METHOD FOR MEASURING THE STATE OF A FLUID

[75] Inventors: Tomoshige Hori, Kitamoto; Kensuke Itoh, Kodaira, both of Japan

[73] Assignee: Snow Brand Milk Products Co., Ltd., Hokkaido, Japan

[21] Appl. No.: 505,354

[22] Filed: Apr. 3, 1990

Related U.S. Application Data

[63] Continuation-in-part of Ser. No. 356,465, May 25, 1989, abandoned, which is a continuation of Ser. No. 5,072, Jan. 20, 1987, abandoned.

[30] Foreign Application Priority Data

Feb. 12, 1986 [JP] Japan ................................ 61-28280

[51] Int. Cl.⁵ .................... G01F 23/24; G01K 13/02
[52] U.S. Cl. .................... 73/295; 73/204.25; 338/24; 364/571.03; 374/136
[58] Field of Search ............ 73/295, 204.19, 204.25, 73/204.27; 374/114, 56, 43, 21, 27, 136, 143

[56] References Cited

U.S. PATENT DOCUMENTS

| | | | |
|---|---|---|---|
| 3,068,693 | 12/1962 | Ferran et al. | 73/204 R |
| 3,921,450 | 11/1975 | Pfister | 73/295 |
| 4,244,217 | 1/1981 | Ledbetter | 73/204.19 |
| 4,408,902 | 10/1983 | Peuker | 374/27 |
| 4,513,616 | 4/1985 | Bezard et al. | 73/295 |
| 4,825,383 | 4/1989 | Ory | 73/295 |

OTHER PUBLICATIONS

"Heated Sensor Finds Wide Application in Fluid Flow Measurements," CGS/Datametrics, Bulletin 600, 1971, 23 pages.
Review of Scientific Instruments, vol. 46, No. 2, Feb. 1975, pp. 185-191 (By S. Firasat Ali).

*Primary Examiner*—Daniel M. Yasich
*Attorney, Agent, or Firm*—Griffin, Branigan & Butler

[57] ABSTRACT

The temperature of one or several sensors which are electrically heated or cooled to a temperature substantially different from a stagnant or running fluid surrounding the said sensor or sensors by applying an electric current to the said sensor or sensors, and the temperature of the said fluid are measured simultaneously to calculate the temperature difference between the said sensor or sensors and the said fluid at an equilibrium state of heat transfer at the surface of the said sensor or sensors, thereby measuring a change in state of the said fluid collectively on an in-line processing basis without disturbing the said fluid; a change in this state results in a change in heat transfer coefficient at the surface of the said sensor or sensors, the coefficient being collectively correlated with the viscosity, density, specific heat, thermal conductivity, thermal diffusivity, coefficient of volumetric expansion, flow speed or flow direction of the said fluid at a given temperature.

8 Claims, 8 Drawing Sheets

TIME

METHOD FOR MEASURING THE STATE OF A FLUID

This application is a continuation-in-part of U.S. patent application Ser. No. 0,356,465 filed on May 25, 1989, now abandoned which application inturn is a continuation of U.S. patent application Ser. No. 005,072 filed on Jan. 20, 1987, and now abandoned.

BACKGROUND TO THE INVENTION

This invention relates to a method for measuring the state of a fluid and, more particularly, to a fluid state measuring method capable of collectively measuring a change in state of a stagnant or running fluid on an in-line processing basis.

The term "fluid" as used in the present specification means all kinds of fluid, i.e., a gaseous substance, a liquid substance or a solid substance such as powder, or of two or more of these substances, as well as a fluid of the type whose phase changes with time, and wherein a "change in state" of the fluid is represented by a change in the viscosity, density, specific heat, thermal conductivity, thermal diffusivity, coefficient of volumetric expansion, flow speed or flow direction of the fluid.

Direct measurement of the viscosity, density and other parameters is very important for process control in a variety of industrial fields that handle fluids, and is especially indispensable for process automation. For determining fluid viscosity, which is one of the most important indices representative of the state of the fluid, a rotational viscometer is most widely used. With the rotational method, the force or torque required for a cylinder to rotate at a constant rate in the fluid is measured in a conventional manner. Another method is based on measurement of the pressure difference between an inlet port and outlet port of a narrow pipe when a predetermined amount of fluid which is practically free of any solids matter such as dust passes through this pipe. However, these mechanical methods have been practised in only limited industrial, medical or academical fields, and their widespread applications to general in-line process control or measurement for fluids has not been realized. This is firstly because the structure of semi-solid fluids such as food gels is destroyed when these mechanical measurements are performed, and secondly that highly viscous fluids display a rate-dependent behavior such that the mechanical methods may only be applied to clean, low viscosity fluids.

In practical processes or measurements, however, such a clean, low viscosity fluid is exceptional and there are a variety of fluids, including liquid systems, which contain highly viscous slurries, printing inks or food gels, whose apparent viscosity is decreased by stirring. When a system contains bubbles whose diameter changes with time, or when a gaseous system contains water droplets in suspension, or when a liquid system contains a colloid such as oil droplets and/or small matter like colloidal metal particles, the conventional methods are not usable. Therefore, the direct measurement of fluid viscosity, or of a collective and characteristic fluidity value representative of viscosity, for the purpose of automatic process control in a practical industrial process has been difficult to achieve.

New methods for measuring fluid viscosity have recently been proposed which are different in principle from the conventional mechanical methods. One method appearing in Japanese patent application Laid-open No. 59-217162 (U.S. Pat. No. 4,611,928) can examine the curd state of milk during a milk-curdling process by inserting a thin metal wire into the milk and measuring the temperature of this thin metal wire in relation to time while applying an electric current intermittently or continuously to the thin metal wire. This method is based on the principle of detecting milk curdling as a function of the change in viscosity of the milk on the basis of a temperature rise in the electrically heated metal wire. In another method proposed in Japanese patent application Laid-open No. 60-152943 (U.S. Pat. No. 4,578,988), a change in the property of a liquid or semi-solid substance is measured by inserting a thin metal wire into the said substance and applying an electric current intermittently or continuously to the thin metal wire. The difference in temperature between the hot metal wire and the fluid surrounding the wire is kept constant with time. The value of the electric current to maintain that constant temperature difference is measured, and a coefficient of heat-transfer at the surface of the wire is calculated on the basis of the measured electric current, the electrical resistance of the wire, the surface area of the wire and the temperature difference kept at a constant known value. Thus, this method for calculating a characteristic value of the fluid is based on the amount of electric current applied to the wire.

These proposals are, however, directed to measuring the viscosity of a specific fluid such as stagnant or substantially stagnant liquid, whose composition and phase do not change, and their widespread applications to general process control and academic measurements for various kinds of fluid cannot be realized without difficulties. Furthermore, in many applications of actual process control, the in-line measurement of quantities which collectively reflect the state of a fluid may depend on all the parameters of viscosity, density, specific heat, thermal conductivity, thermal diffusivity, coefficient of volumetric expansion, flow speed or flow direction of the fluid, etc. These quantities may be of more significance for accurate measurement than a specified characteristic value indicative of viscosity only. Therefore, the conventional mechanical methods are totally unsuited for such collective measurements.

BRIEF DESCRIPTION OF THE INVENTION

A hot-wire technique that applies the heat-transfer phenomenon has been applied for the measurement of fluid viscosity, which is related to the progress of milk curd formation. With fluids of different viscosities, the rate of convective heat transfer to each fluid at the surface of the hot-wire probe differs, the heat being more slowly transferred the higher the viscosity of the fluid is, so that the temperature of the built-in hot wire in the probe at the equilibrium temperature will be correspondingly higher. This is because a higher viscosity fluid will possess a thicker boundary layer around the probe in the equilibrium state.

The thermal conductivity of a liquid has normally been calculated from the initial stage of the logarithmic time vs. temperature-difference curve (the difference in temperature between the surface of a hot wire and the stagnant fluid surrounding the wire) by what is called the transient hot-wire method. Little attention, however, has been paid to the subsequent stage during which the curve reaches equilibrium. In the initial phase of this time vs. temperature curve, heat is transferred by conduction, while in the phase up to equilibrium, heat is transferred mainly by both conduction and convection.

Laminar free-convection heat transfer at the equilibrium state is generally given by the following equation:

$$f(Nu, Gr, Pr, Re) = 0 \quad (1)$$

where $$Nu = \frac{\alpha L}{\lambda} \quad (2)$$

$$Gr = \frac{L^3 g \beta (\theta_s - \theta_\infty)}{v^2} \quad (3)$$

$$Pr = \frac{v}{a} \quad (4)$$

$$Re = \frac{uL}{v} \quad (5)$$

and where L is a characteristic length and g is the gravitational acceleration.

Substitution of Eqs. 2-5 into Eq. 1 yields Eq. 6, which indicates that the first four physical properties of kinematic viscosity $v$, thermal conductivity $\lambda$, thermal diffusivity $a$, coefficient of volumetric expansion $\beta$, and velocity u of a fluid in the formula can be correlated with the other three heat-transfer characteristics of heat-transfer coefficient $\alpha$, surface temperature $\theta_s$, and fluid temperature $\theta_\infty$.

$$f(v, \lambda, a, \beta, u, \alpha, \theta_s, \theta_\infty) = 0 \quad (6)$$

Of the three heat-transfer characteristics in Eq. 6, fluid temperature $\theta_\infty$ can be measured by the conventional method. In addition, the other two characteristics, $\alpha$ and $\theta_s$, for a vertical hot wire can be given as a function of the measurable variables.

Fourier's equation for steady-state heat conduction in a vertical cylinder, in which heat W is being generated in a unit volume of the cylinder, $$\nabla^2 \theta = -\frac{W}{\lambda_w} \quad (7)$$

leads to the analytical solution $$\theta(r) = -\frac{W}{4\lambda_w} r^2 + \theta_s + \frac{Wd^2}{16\lambda_w} \quad (8)$$

for $|r| < d/2$ under the following boundary conditions:

$$\left(\frac{\partial \theta}{\partial r}\right)_{r=0} = 0 \quad (9)$$

$$\theta\left(\frac{d}{2}\right) = \theta_s \quad (10)$$

Integration of Eq. 8 between r=0 and d/2 as $$\theta_w = \frac{1}{\pi \left(\frac{d}{2}\right)^2} \int_0^{d/2} 2\pi r \theta(r) dr \quad (11)$$

gives $$\theta_s = \theta_w - \frac{Wd^2}{32\lambda_w} \quad (12)$$

where $$W = \frac{R_w I_w^2}{\pi \left(\frac{d}{2}\right)^2 l} \quad (13)$$

$$R_w = R_o + R_1 \theta_w + R_2 \theta_w^2 \quad (14)$$

$$\lambda_w = \lambda_o + \lambda_1 \theta_w \quad (15)$$

$$R_w = \frac{V_w}{I_w} \quad (16)$$

for a hot wire (diameter=d and length=l) made of a thin metal filament such as platinum. Therefore, the surface temperature is a function of measurable values, which are the average hot-wire temperature, $\theta_w$, and the heat generated in a unit length of the wire, Q:

$$\theta_s = \theta_w - \frac{Q}{8\pi \lambda_w} \quad (17)$$

$$= f(\theta_w, Q) \quad (18)$$

$$Q = \frac{R_w I_w^2}{l} \quad (19)$$

where r is the radial distance along the diameter of the hot wire, $\lambda w$ is the thermal conductivity of the hot wire, $\theta w$ is the temperature of the hot wire, Rw is the electrical resistance of the hot wire, $R_0$, $R_1$ and $R_2$ are temperature coefficients of electrical resistance, $\lambda_0$ and $\lambda_1$ are the temperature coefficients of thermal conductivity, Vw is the voltage across the hot wire, and Iw is the electric current applied to the hot wire.

By definition, the heat-transfer coefficient at the surface of a hot wire is $$\alpha = \frac{Q}{\pi d (\theta_s - \theta_\infty)} \quad (20)$$

Hence $$\alpha = f(\theta_s - \theta_\infty, Q) \quad (21)$$

$$= f(\theta_w - \theta_\infty, Q) \quad (22)$$

Thus, from Eqs. 12-22, conventional measurement of the fluid temperature and voltage between the two ends of a hot wire can result in all three characteristic values of $\alpha$, $\theta s$ and $\theta w$ in Eq. 6. Moreover, temperature difference $\theta_w - \theta_\infty$ can describe the overall state of the fluid when the heat generation in the wire, Q, is kept practically constant with time.

BRIEF DESCRIPTION OF THE DRAWINGS

The set of temperature differences for the x, y and z axes shown in FIGS. 3A, 3B and 3C illustrates the change in flow direction of a fluid measured by using a fluid temperature detector and three hot-wire probes, whose longitudinal axes x, y and z are orthogonal to each other. The said detector and three hot-wire probes are all fixed in the same fluid to be measured.

FIG. 9A shows in-line data collected from an industrial cheese-making process. Both the hot-wire probe and electrical resistor for temperature detection are mounted on the tank to which fresh milk is being distributed, and changes in the temperatures of the built-in hot-wire resistor, $\theta w$, fluid temperature, $\theta_\infty$, and temperature difference between these two, $\Delta\theta w$, monitor the whole process of curdmaking in the cheese industry.

DESCRIPTION OF THE INVENTION

Before describing the preferred embodiment of the invention, a brief summary of the overall invention is set forth below in connection with FIGS. 5A, 5B, 6A, 6B, 7A, 7B, 8, 10, 11, 12 and 13.

Figure 8:
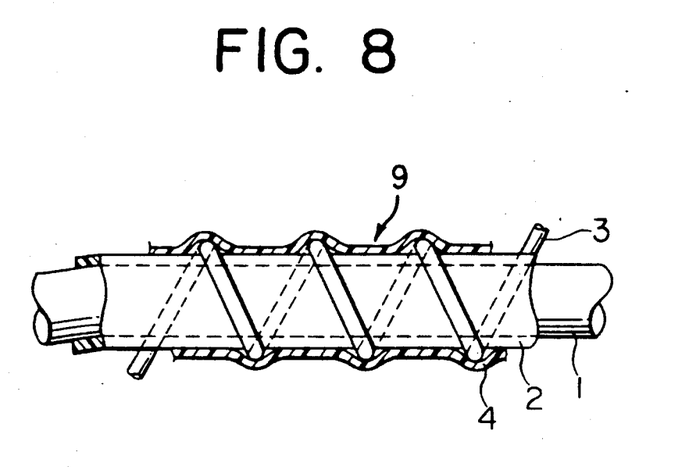
FIG. 8 is a cut-away illustration showing an example of the hot-wire probe.
Figure 10:
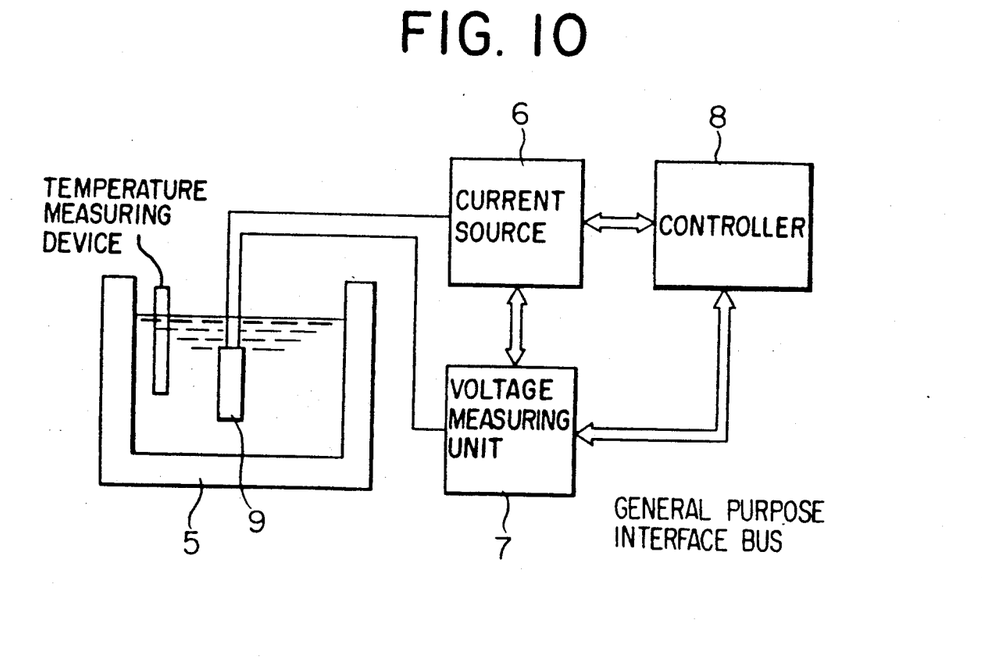
FIG. 10 is a schematic block diagram showing an example of a measuring system. Connection of the electrical lead wires and interface bus are shown in a simplified manner.
Figure 12:
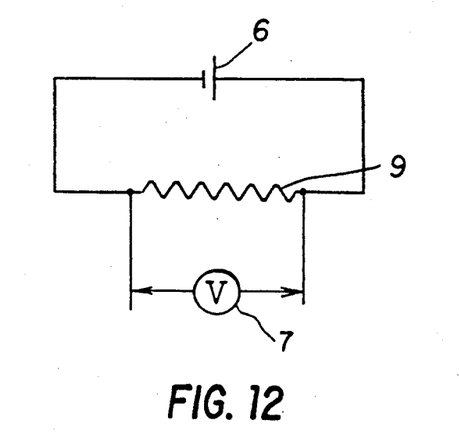
FIG. 12 is a circuit diagram for measuring the electrical resistance of the built-in resistor in the hot-wire probe.
Figure 13:
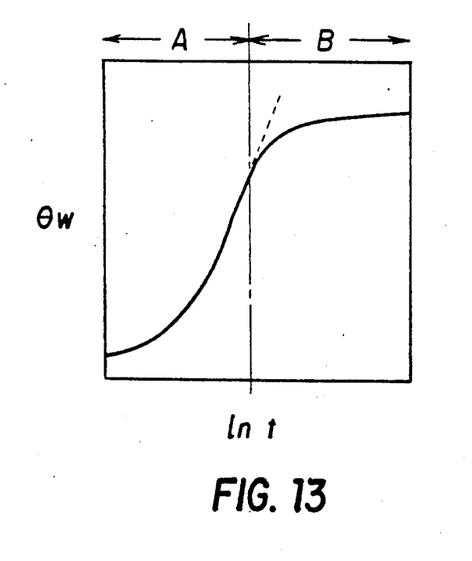
FIG. 13 is an illustrative relationship between the logarithmic time vs. hot-wire temperature resulting from transient heat transfer in the initial linear porion of the time vs. hot-wire temperature curve, and in the subsequent portion in which heat is transferred mainly by both conduction and convection.

As shown in FIG. 10, tank 5 contains a fluid whose state is to be determined. In that fluid, a sensor element 9, which is referred to hereinafter as a hot-wire probe, and four electrical lead wires connect that probe to electric current source 6 and voltage measuring unit 7. Of the four electrical lead wires, two of them are connected to one end of the electrical resistor built into the hot-wire probe, and the other two are connected to the other end of the same electrical resistor. Thus, four electrical lead wires are connected to the hot wire probe. The connection of these four electrical lead wires to electric current source 6 and voltage measuring unit 7 is shown in FIG. 12. Controller 8 is connected to current source 6 and voltage measuring unit 7. An example of the hot-wire probe 9 is shown in FIG. 8, where 1 is a stainless steel metal rod, 2 is an electrical insulator, 3 is a platinum wire wound around rod 1, and 4 is an electrical insulator. In addition, a conventional sensor for measuring the temperature of the fluid in tank 5 is used in a suitable manner. The hot-wire probe can be used for this purpose when the electric current applied to it is sufficiently small. One mA is recommended as such a small current for fluid temperature measurement. Although only one hot-wire probe is illustrated in the tank shown in FIG. 10, in actual applications several probes will be mounted on the same tank, each probe being connected to electric current source 6 and voltage measuring unit 7 in the same manner as that already described.

The hot-wire probe in a stagnant fluid or in a fluid running at a constant rate shows an equilibrium temperature just after the electric current has been applied to the hot-wire probe from current source 6. The heat electrically generated in the hot-wire probe is transferred to the fluid surrounding the hot-wire probe only by conduction during initial stage A in FIG. 13 or during the initial linear portion of the logarithmic time vs. temperature curve in FIG. 13, while in the subsequent stage, the heat is transferred mainly by both conduction and convection. The temperature of the hot-wire probe and built-in resistor reach equilibrium at a given fluid temperature when heat is transferred by both conduction and convection, which is shown during stage B of FIG. 13. This equilibrium temperature of the hot-wire probe is directly correlated with the overall fluid state such as viscosity, density, specific heat, thermal conductivity, thermal diffusivity, coefficient of volumetric expansion, flow speed and flow direction of the fluid. This equilibrium temperature of the hot-wire probe is referred to hereinafter as $\theta w$.

The difference between the equilibrium temperature of hot-wire probe 9 and the temperature of the fluid in tank 5 is sufficient in many systems to deduce the state of the fluid. The temperature of hot-wire probe 9 alone is not applicable to accurately deduce the state of the fluid for most practical systems, in which the fluid temperature normally varies with time. Thus, with the present invention, the bulk temperature of the fluid in tank 5 must also be measured, and the difference between that temperature of the fluid and the equilibrium temperature of hot-wire probe, $\Delta\theta w$, is thus known. The temperature of the fluid can be determined by any convenient conventional means; e.g., by placing in the fluid a thermocouple or a conventional electrical resistor for temperature detection, which can be connected to voltage measuring unit 7 in a conventional manner, and controller 8 will then calculate the temperature difference in a known manner.

Figure 5A:
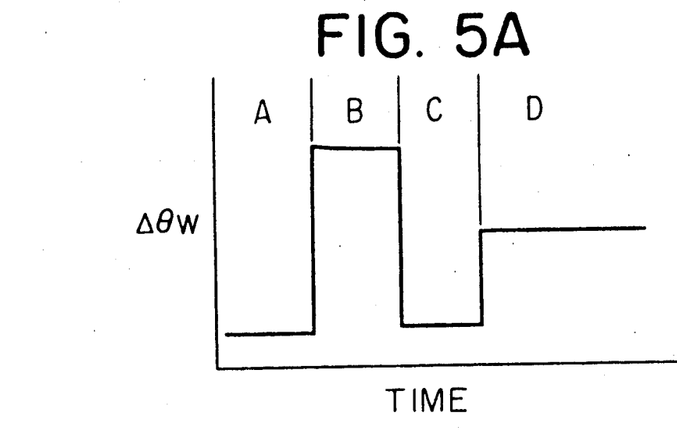
FIGS. 5A and 5B respectively illustrate the relationship of the temperature difference $\Delta\theta w$ measured for a liquid (regions A and C in FIG.1 5A), gas (region B) and a mixture of both gas and liquid (region D), and the relationship of the temperature of the liquid, gas or gas/liquid, again each with respect to time.
Figure 5B:
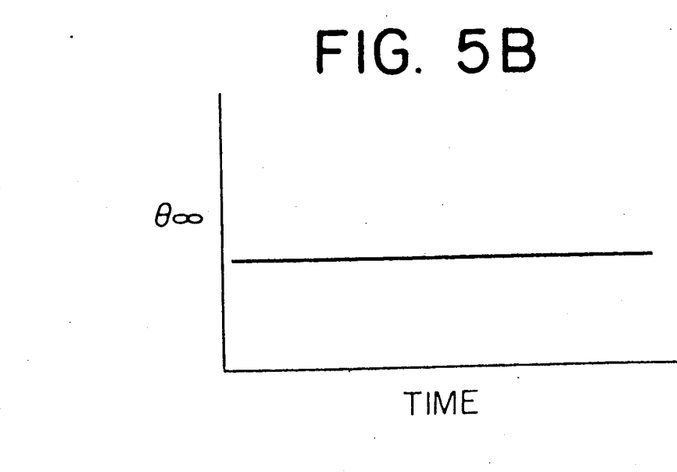

Temperature difference $\Delta\theta w$ can then be used to deduce the state of the fluid. This deduction is illustrated in FIGS. 5A and 5B in regard to the relatively simple system of a liquid/gas/liquid-gas. As shown in FIG. 5B, the temperature of the fluid in this relatively simple system is constant with time. In FIG. 5A, the temperature difference in region A is relatively small. This indicates heat transfer from hot-wire probe 9 to the fluid at a relatively high rate, from which it can be deduced that the fluid in tank 5 is now a liquid. In region B, the temperature difference is relatively large. This indicates heat transfer from hot-wire probe 9 to the fluid at a lower rate, from which it can be deduced that the fluid in tank 5 is now a gas. In region C, the temperature difference is again small, which suggests that the fluid in tank 5 is again a liquid. Finally, in region D, the temperature difference is somewhere between the $\Delta\theta w$ value for a liquid and a gas, from which it can be deduced that the fluid in tank 5 is now a mixture of a liquid and a gas.

Figure 6A:
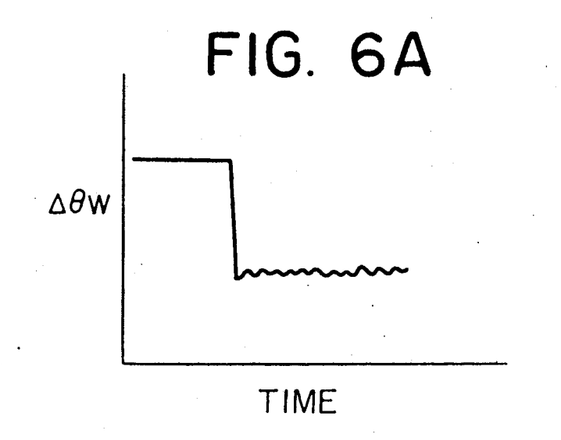
FIGS. 6A and 6B respectively illustrate the relationship of the temperature difference $\Delta\theta w$ and the bulk fluid temperature with respect to time. The abrupt decrease in the time vs. temperature-difference curve in FIG. 6A when the bulk fluid temperature is kept constant with time as shown in FIG. 6B indicates the critical point after which the onset of turbulent flow occurs in the fluid.
Figure 6B:
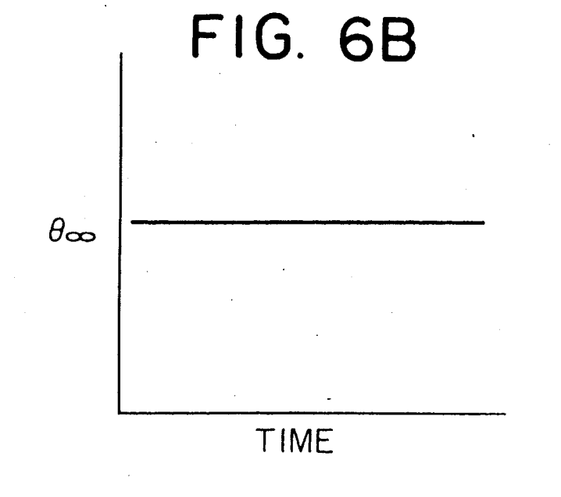
Figure 7A:
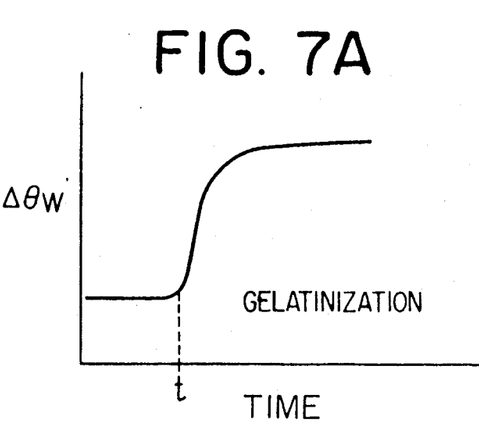
FIGS. 7A and 7B respectively illustrate the nondestructive detection of milk curd formation. Although the fluid temperature varies with time, the temperature difference $\Delta\theta w$ characterizes the onset of milk clotting and the subsequent process of milk curd formation.
Figure 7B:
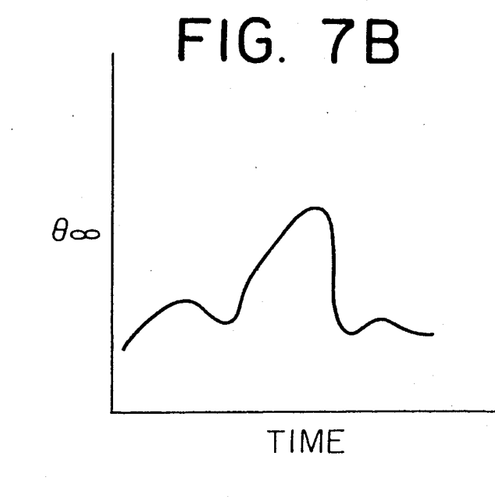
Figure 11:
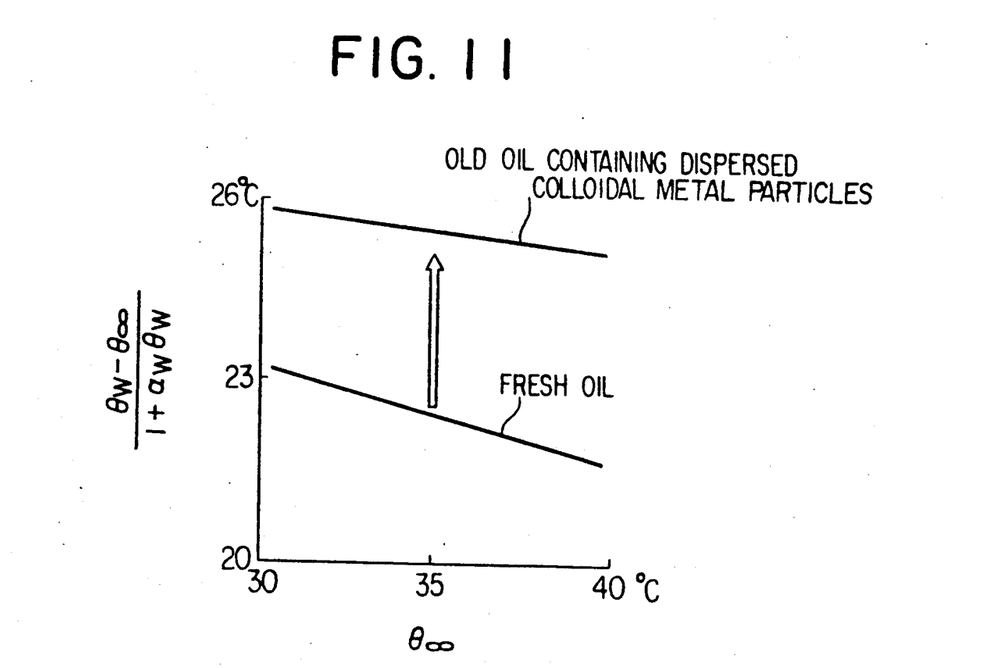
FIG. 11 is a graph illustrating the effect of the fluid temperature, amount of dispersed colloidal metal particles, and the freshness or amount of the lower boiling-point components which were lost because of vaporization during their specific use in the process.

The foregoing description illustrates the invention in summary form and some of the preferred embodiments of the invention, which are described in detail hereinafter. However, the invention is not limited to such simple systems, and is applicable to more complex systems. FIGS. 6A and 6B show that the invention can determine the flow state of a fluid, i.e., whether the flow of the fluid is laminar at a slower rate (the initial equilibrium portion of the time vs. temperature difference curve in FIG. 6A) or turbulent at a faster rate (the subsequent portion with some irregularity in FIG. 6A). FIGS. 7A and 7B illustrate the detection of the progress of gel formation. The change in viscosity can be detected even when the fluid temperature varies with time as shown in FIG. 7B. FIG. 11 indicates the difference in heat transfer characteristics at the surface of hot-wire probe 9 fixed in a fresh mineral oil and in an older mineral oil in which colloidal metal particles are dispersed. This change in index value indicated on the y axes mainly originates from the increasing apparent viscosity of the sample oils. The example of a practical index value shown in FIG. 11 is the temperature difference normalized with the change of heat flux at the surface of the probe due to the change induced in the hot wire to which a constant electric current is applied.

However, in more complex systems, simple imformation based on a read-out of the temperature-difference index is not sufficient to deduce the state of the fluid in a profitable manner. Additional information resulting from both hot-wire measurement and related properties such as the fluid temperature, rate of change of fluid temperature with time, thermal conductivity, and the state of flow is required. Properties other than viscosity may be used in this regard. For example, multiple hot-wire probes 9 can be used in tank 5. When three hot-wire probes are disposed in tank 5 with their longitudinal axes oriented orthogonally to each other and the fluid in tank 5 is being agitated, a profile of the flow in the fluid can be obtained. This is, of cource, useful in deducing the state of the fluid.

DESCRIPTION OF THE PREFERRED EMBODIMENTS

The preferred embodiments of the invention will now be described by way of example with referrence to the accompanying drawings.

A conventional temperature measuring sensor such as an electrical resistor for temperature detection is fixedly supported in a stagnant or running fluid to measure the fluid temperature, $\theta_\infty$. At the same time, a single hot-wire probe, or multiple hot-wire probes whose longitudinal axes are oriented in different directions, are immersed and fixedly supported in the same fluid surrounding the said hot-wire probe or probes, and their contour surfaces are heated or cooled to a temperature significantly different from the bulk fluid temperature. Temperatures $\theta wi$ of the hot-wire probes, where $i=1$ to n with n being the number of hot-wire probes, are measured while thermally contacting the hot-wire probe by the fluid surrounding the probe. Absolute values of temperature differences between the fluid and hot-wire probes denoted by $\Delta\theta wi = \theta wi - \theta_\infty$ for $i=1$ to n are calculated. Measurement of the values for $\theta_\infty$ and $\theta wi$ and a comparison between these values for obtaining the $\Delta\theta wi$ value are carried out in relation to time to collectively monitor the state of the fluid. As any shape for the hot-wire probe can be used when the heat-generating source or heat-absorbing source is built into the probes, the temperature of this source can be measured directly and in real time.

For theoretical considerations, the hot-wire probe is recommended to be rod-like or plate-like, including a thin metal wire, a ceramic rod with a built-in electrical resistor, a ceramic plate printed with a platinum wire pattern, a platinum wire or coil molded with heat-proof resin or ceramic powder and surrounded by a stainless steel cover pipe or cover plate, or a heat absorbing element based on the Peltier effect which is embedded in a pipe or plate that protects the element from chemical or physical damages by the process.

Figure 1A:
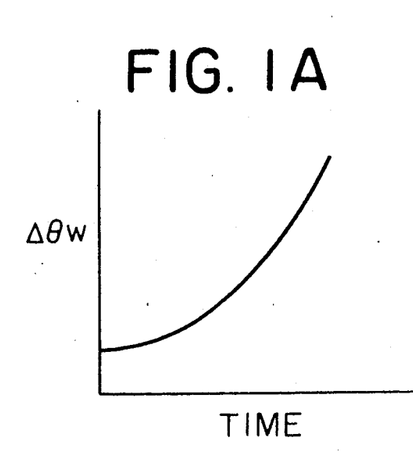
FIGS. 1A and 1B respectively illustrate graphs showing the relationship of the temperature difference, $\theta w - \theta_\infty$, between the fluid and built-in hot-wire resistor, and the relationship of kinematic viscosity $v$ of the fluid, each with respect to time, when the other four variables $\lambda$, $\beta$, a and u are practically constant. The temperature difference is referred to hereinafter as $\Delta \theta w$.
Figure 1B:
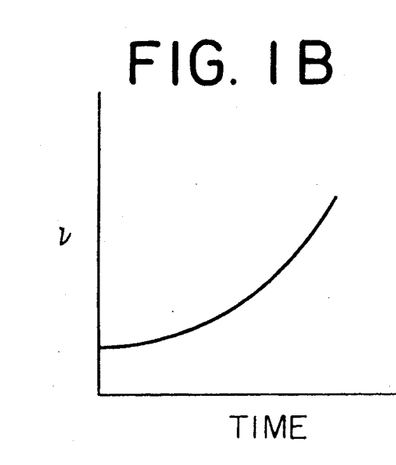
Figure 2A:
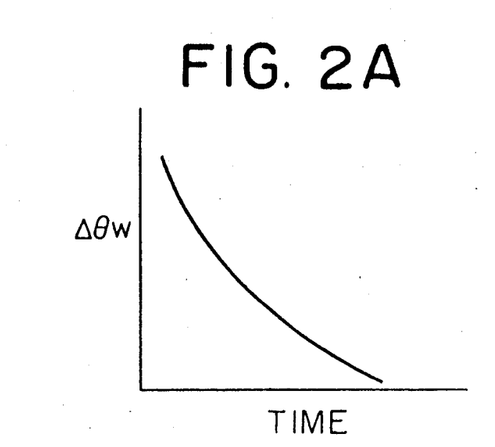
FIGS. 2A and 2B respectively illustrate the relationship of the temperature difference $\Delta\theta w$ between the fluid and built-in hot-wire resistor, and the relationship of flow speed u of the fluid, each with respect to time.
Figure 2B:
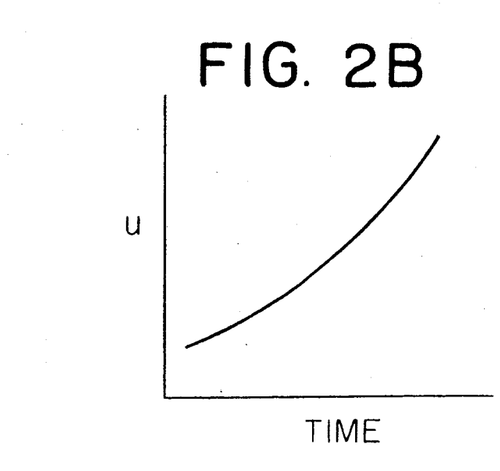

Index value $\Delta\theta wi$ has, on the one hand, a positive correlation with kinematic viscosity $v$ of the surrounding stagnant fluid or that of the fluid running at a constant rate with time both on the same time base when only the kinematic viscosity increases with time, which is shown in FIGS. 1A and 1B. On the other hand, it has a negative correlation with flow velocity u of the fluid whose kinematic viscosity is constant with time as shown in FIGS. 2A and 2B when only the velocity increases with time.

Figure 3A:
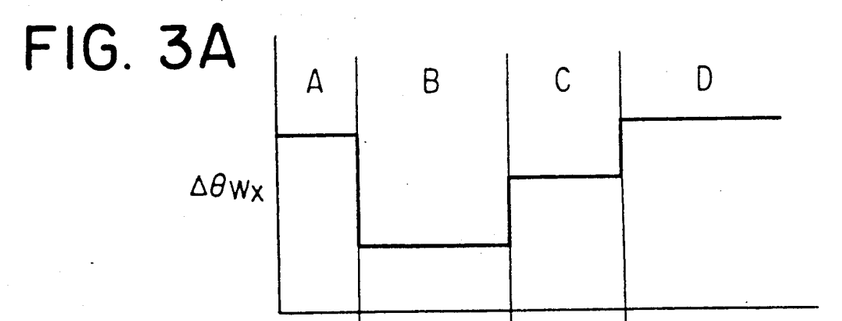
Figure 3B:
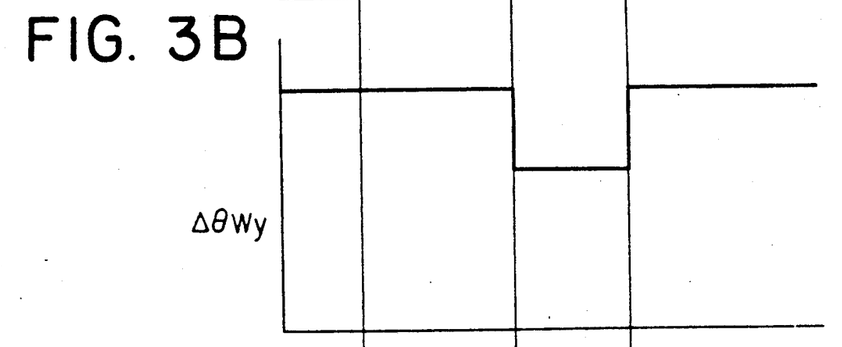
Figure 3C:
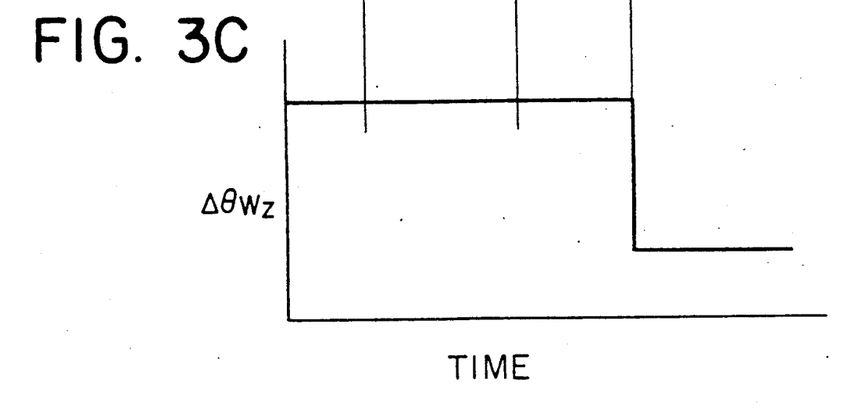

When $n=3$ and three rod-like hot-wire probes are arranged with their longitudinal axes oriented orthogonally to each other, the flow direction can be detected on the basis of temperature differences $\Delta\theta wx$, $\Delta\theta wy$ and $\Delta\theta wz$, which are respectively related to the orthogonal coordinate components of the x, y and z axes of the said flow of the liquid, as indicated in FIGS. 3A, 3B and 3C. These figures will result in a collective examination of the running fluid surrounding the said three hot-wire probes, provided that in region A in FIGS. 3A-3C there is no flow in any direction in the fluid, there is a flow only in the x direction in region B, there is a flow both in the x and y directions in region C, and there is a flow in the z direction, respectively.

Figure 4A:
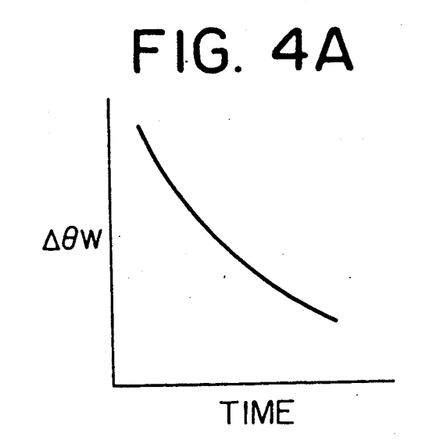
FIGS. 4A and 4B respectively illustrate the relationship of the temperature difference $\Delta\theta w$ between the built-in hot-wire resistor and a fluid containing colloidal metal particles of higher thermal conductivity than the fluid, and the amount of these particles, each with respect to time.
Figure 4B:
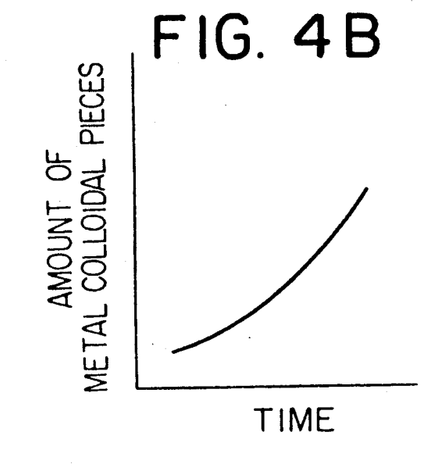

If substances of different thermal conductivity, density or the like such as colloidal metal particles or small bubbles are dispersed in the fluid, a significant change in the $\Delta\theta wi$ value can be monitored, having a significant correlation with the amount of colloidal metal particles as shown in FIGS. 4A and 4B, in spite of the fact that the apparent change in viscosity of the fluid as a whole is small.

Since kinematic viscosity $v$ is defined as $$v = \mu/\rho \tag{23}$$

where $\mu$ is the viscosity and $\rho$ is the density, and $\Delta\theta wi$ reflects $v$ as has been explained with reference to FIGS. 1A and 1B, the value of $\Delta\theta wi$ is large for a fluid in the form of a gas, is relatively small for a fluid in the form of liquid having relatively large $\rho$, and is intermediate as indicated by region D in FIG. 5A for a system in which a gas and liquid are coexistent as a mixture of these two. Thus, as shown in FIG. 5A, region A in FIG. 5A is for a liquid, region B for a gas, region C for a liquid, and region D for a mixture of liquid and gas such as a cloud in the sky. It should be noted that the values indicated in FIG. 5A were obtained under the condition that bulk fluid temperature $\theta_\infty$ remains constant with time as shown in FIG. 5B.

When the hot-wire probe has a small time constant, the $\Delta\theta w$ value is subjected to variations with time, indicating a small flow stream whose direction and flow rate varies with time, which resembles the turbulent flow that is often observed in a general process fluid. Accordingly, an undulation associated with the time vs. $\Delta\theta w$ curve illustrated in FIG. 6A, under the condition that fluid temperature $\theta_\infty$ remains constant with time as shown in FIG. 6B, indicates the onset of turbulent flow. If, under the condition that fluid temperature $\theta_\infty$ is arbitrarily time-variable as shown in FIG. 7B and that $\Delta\theta w$ is not subjected to any variations indicative of the onset of turbulent flow, the value of $\Delta\theta w$ increases, an increase in viscosity $\mu$ representing, for example, gelling of liquid, which can be monitored from a time vs. $\Delta\theta w$ curve as shown in FIG. 7A where gel formation starts at time t.

In general, the measured change in $\Delta\theta w$ value is directly correlated with the collective state of the fluid, which can be expressed as a function of the kinematic viscosity, thermal conductivity, thermal diffusivity, coefficient of volumetric expansion, direction of flow, and rate of flow of the fluid. That is, the $\Delta\theta w$ measurement describes the overall change in the physical properties of the fluid even if the flow is stopped, while discrimination of the effect of each property can be made when the values of the other properties are known in advance or are assumed to be constant in the process. In any respect, the $\Delta\theta w$ value measured by using the present invention can practically indicate the existing state or overall flowability of the fluid in a process directly, simultaneously and in line without disturbing the stagnated or running fluid.

The invention is described by referring to the following experimental examples.

EXAMPLE 1

A hot-wire probe for use in a curdmaking tank of 15 tons in volume comprises, as shown in FIG. 8, stainless steel rod 1 covered with electrically insulating member 2 of Teflon ® (polytetrafluoroethylene), thin platinum wire 3 of diameter 0.1 mm wound around member 2, and electrically insulating member 4 of Teflon ® (polytetrafluoroethylene) covering the platinum wire winding. The built-in platinum wire has an electrical resistance (Ro at 0° C.) of 3.6172 Ω, a temperature coefficient of this resistance ($\alpha w$) of 0.008817 1/° C., and a heat-generating portion in the hot wire probe of 5 cm in length along stainless steel rod 1. The temperature measuring system shown in FIG. 10 was employed to continuously measure the temperature of the hot platinum wire built into the probe. This measuring system comprised tank 5, current source 6, voltage measuring unit 7, controller or computer 8, and hot-wire probe 9. An electrical resistance device for temperature detection, which is not shown in FIG. 10, is also fixed in tank 5.

The temperature of the hot platinum wire ($\theta w$) was calculated by using the following formulae:

$$\theta w = (Rw/Ro - 1)/\alpha w \tag{24}$$

$$Rw = Vw/Iw \tag{25}$$

$$\alpha w = R1/R2 \tag{26}$$

where Rw is the electrical resistance of the built-in hot wire, Vw is the measured voltage across the built-in hot wire, and Iw is the direct electric current applied to the built-in hot wire, 0.4 A in this example. The temperature ($\theta_\infty$) of the surrounding fluid in the tank (which could be air, water vapor, milk, milk curd, whey, hot water, cleanser and the like) was measured by using a conventional electrical resistance device for temperature detection. Therefore, temperature difference $\Delta\theta w$ could be calculated.

Figure 9A:
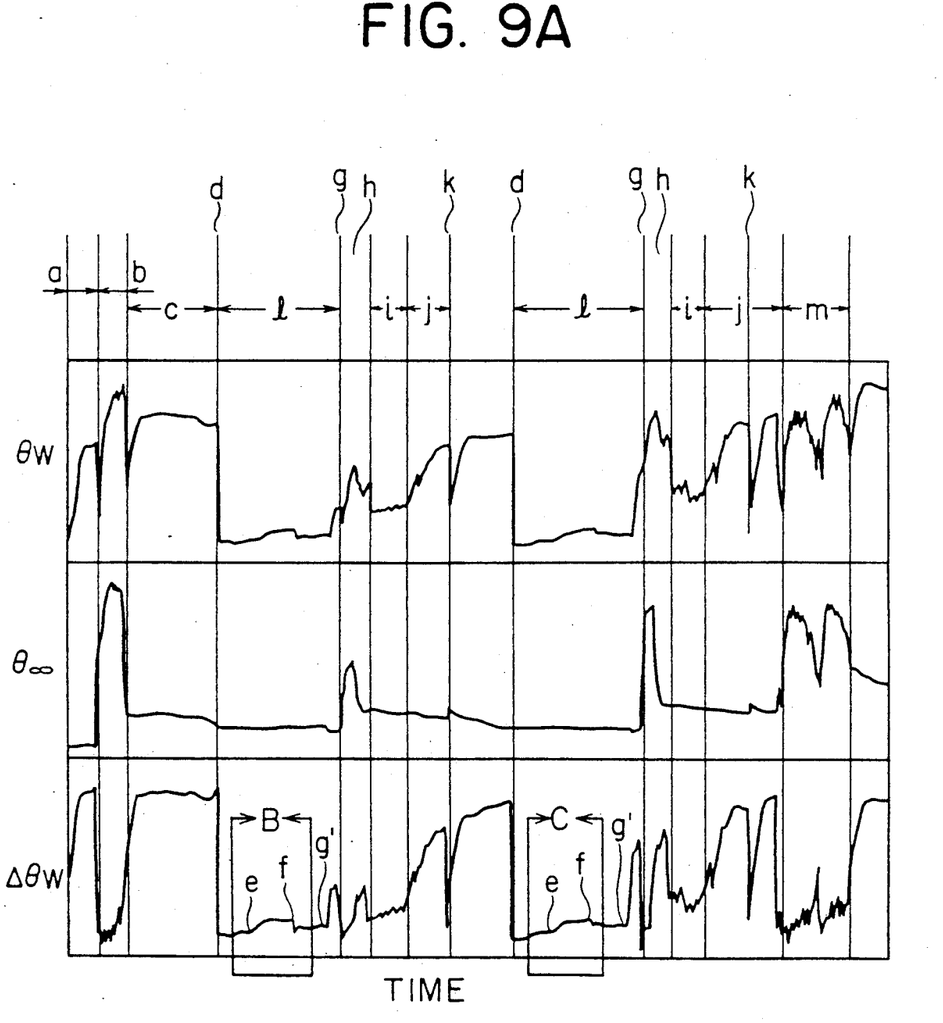
Figure 9B:
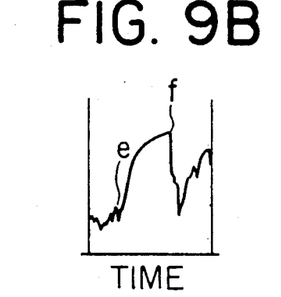
FIGS. 9B and 9C are enlarged illustrations of portions B and C in FIG. 9A with the $\Delta\theta w$ ordinate more enlarged in scale than the abscissa.
Figure 9C:
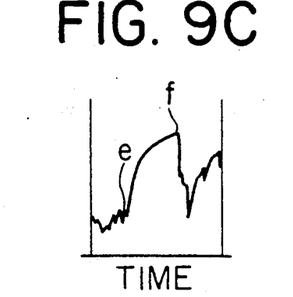

Three characteristic values ($\theta w$, $\theta_\infty$ and $\Delta\theta w$) monitored the whole process of curdmaking in the cheese industry continuously and in line. These measured results are shown in FIGS. 9A, 9B and 9C. When the tank was initially empty and the fluid was gas or wet air at room temperature, as is usual early in the morning in a cheese factory, the temperature-difference resulted in a higher value as shown in regions a and c in FIG. 9A. The temperature difference is much lower when the fluid was a liquid or hot water in region b in FIG. 9A. In this region, the hot water was sprayed into the tank for sterilization. These changes in the specific temperature-difference value between regions a, b and c resulted from a change in the kinematic viscosity of the fluid, i.e., mainly because the kinematic viscosity of air or a gas is generally much larger than that of water or a liquid.

The progress of milk curd formation is indicated in portions b and c in FIG. 9A, and enlarged traces are illustrated in FIGS. 9B and 9C. In these portions, point e indicates the onset of milk clotting, which was followed by an enzymatic reaction (between point d and e in FIG. 9A) when the viscosity of the milk increases abruptly because of its coagulation. The progress of milk curd formation is shown as the time vs. temperature-difference curve between points e and f. The abrupt decrease of the temperature-difference value at point f reflects the effect of heat transfer by forced convection. The milk coagulum was cut at this point f, and the coagulated fluid was forced to move in the tank while the hot-wire probe recording the effects. Therefore, the onset of forced convection heat transfer was monitored at this point f.

At point g′ in FIG. 9A, stirring of the mixture of liquid whey and semisolid curd granules was stopped, and at point g, part of the separated whey was discharged to lower the fluid level in the tank. After this process in region h, the hot-wire probe is partly open to wet air, and the kinematic viscosity increased to cause an increase of the temperature-difference value. Region i is a mixing process where the mixture of liquid whey and semi-solid milkcurd granules was agitated in the tank. The probe was partly open to wet air and partly immersed into the liquid. These changes with a shorter time interval in the process were monitored as a variation of the temperature-difference value shown in region 1 in FIG. 9A. Region j indicates the lowered level of the remaining mixture of liquid and semi-solids. At point k, the hot-wire probe was cleaned with a shot of water at high pressure. The two peaks of the hot-wire temperature in region m resulted from the final cleaning in place process of the day, where hot alkaline and acid cleanser liquids were sprayed on the inside walls and bottom of the tank and onto the hot-wire probe fixed inside of tank.

In this manner, various types of change in the state of the fluid within the milk tank during the curdmaking process were collectively monitored from the three measured characteristic values ($\theta w$, $\theta_\infty$ and $\Delta \theta w$) in accordance with the method of the present invention.

EXAMPLE 2

A sensor element in the form of a platinum wire ($R_o = 31.3186 \Omega$ and $\alpha w = 0.008817$ $1/°C$.) having a length of 100 mm and a diameter of 0.1 mm was vertically supported in fresh mineral oil, and otherwise in old used mineral oil in which colloidal metal particles of about 1 $\mu m$ diameter were dispersed at a concentration of 100 ppm. An electric current of 0.7 A was applied to the platinum wire to generate heat in the said wire, and the heat was transferred from the hot-wire to the surrounding fluid mainly by both conduction and convection.

FIG. 11 illustrates that the index value ($|\theta w - \theta_\infty|/(1 + \alpha w \theta w)$) calculated from the measured hot-wire temperature, the bulk oil temperature and the temperature coefficient of electrical resistance of the said sensor wire could characterize the difference in the state of the mineral oil in a temperature range from 30° C. to 40° C. The denominator of the index $(1 + \alpha w \theta w)$ normalizes the change in the heat flux resulting from the change in the hot-wire temperature ($\theta w$) when a constant electric current was applied to the hot-wire The difference appearing in the plot of the fluid temperature vs. the said index resulted mainly from a change in the fluid viscosity, thermal conductivity and their temperature coefficients. The vaporization of the lower boiling-point components from the older mineral oil led to the increase of fluid viscosity, while the increase of the amount of dispersed metal colloids in the older oil resulted in a higher thermal conductivity.

Although particular preferred embodiments of the invention have been disclosed for illustrative purposes, it will be recognized that variations and modifications, e.g., present measurements for melting and flowing resins at high temperature and high pressure, to the disclosed methods lie within the scope of the present invention.

What is claimed for the present invention:

1. A method for determining the physical state of a fluid at a given temperature and pressure, comprising:
   (a) thermally contacting at least one sensor with the fluid;
   (b) supplying an electric current to said sensor to either heat or cool the sensor to a temperature substantially different from the temperature of the fluid, whereby heat transfers between the fluid and the sensor;
   (c) determining the temperature of the sensor and measuring the temperature of the fluid, and calculating the difference in said temperatures;
   (d) calculating the heat transfer between said sensor and said fluid by a heat transfer formula which uses as the essential variable (a) the said temperature difference; or (b) the said temperature difference and the fluid temperature; or (c) an index value, which index value is a function of (a) or (b); and
   (e) comparing the said calculated heat transfer with similar prior calculations of heat transfers of the fluid when in other physical states, so as to determine by said comparison, the physical state of the fluid.

2. The method of claim 1, wherein the sensor comprises (a) a built-in electrical resistor which generates heat by applying an electric current to the resistor or (b) a built-in electrical element which absorbs heat by applying an electric current to the electrical element.

3. The method of claim 2, wherein heat transferred at a surface of the said sensor is kept constant with time.

4. The method of claim 2, wherein the said temperature difference is measured at an equilibrium point.

5. The method of claim 2, wherein the temperature of the said sensor is measured as the average temperature of the built-in heating resistor or built-in electrical element.

6. The method of claim 2, wherein the said temperature of the said sensor is measured as the surface temperature of the said sensor.

7. The method of claims 3 or 4 or 5 or 6, wherein electric current is a direct electric current.

8. The method of claim 1, wherein the said determination of the physical state of the fluid is followed by:
   (a) measuring, predetermining and/or estimating the value of at least one fluid property of viscosity, density, specifice heat, thermal conductivity, thermal diffusivity, coefficient of volumetric expansion, flow speed and flow direction of the said fluid at a given temperature; and
   (b) substituting the said value into the convention heat transfer equation.

* * * * *